US005187075A

United States Patent [19]
Green et al.

[11] Patent Number: 5,187,075
[45] Date of Patent: Feb. 16, 1993

[54] CLONING AND EXPRESSION OF A VARIANT GENE OF PLATELET FACTOR 4 AND COMPOSITIONS THEREOF TO MODULATE IMMUNE RESPONSES

[75] Inventors: Christopher J. Green; Paul H. Johnson, both of Menlo Park, Calif.

[73] Assignee: SRI International, Menlo Park, Calif.

[21] Appl. No.: 302,425

[22] Filed: Jan. 26, 1989

[51] Int. Cl.$^5$ .................. C12N 15/67; C12N 15/03; C12N 15/12; C12P 21/00
[52] U.S. Cl. .................................. 435/69.1; 435/69.7; 435/172.3; 435/71.2; 435/252.3; 435/320.1; 530/380; 536/23.5; 536/23.51; 536/24.1; 536/23.4; 935/45; 935/51
[58] Field of Search ............ 435/69.1, 69.2, 172.3, 435/320.1, 71.2, 69.7; 514/822; 536/27; 530/300, 380

[56] References Cited

U.S. PATENT DOCUMENTS

| | | | |
|---|---|---|---|
| 4,645,828 | 2/1987 | Twardzik | 530/324 |
| 4,702,908 | 10/1987 | Thorbecke | 424/88 |
| 4,897,348 | 1/1990 | Johnson et al. | 435/69.1 |
| 5,026,639 | 6/1991 | Johnson | 435/69.1 |

OTHER PUBLICATIONS

Green, C. J. et al., *The Journal of Cell Biology* 107 (6 part 3): 309A Abstract No. 1743 (1988).
Eisman, et al., "Structural & Functional Comparison of the Genes for Human Platelet Factor 4 & PF4 alt." *Blood*, vol. 76, pp. 336–344, (1990).
Poncz, et al., "Analysis of the Human Platelet Factor 4 Gene Reveals Gene Duplication & A Possible Alternate PF4 (PF4alt) Protein," *Clin. Res.* 36:568a, (1988).
Katz et al., Proc. Nat'l. Acad. Sci. USA vol. 83:3491–3495 (1986).
Taylor et al., Nature vol. 297:307–312 (1982).
Wu et al., Preparative Biochemistry vol. 7:6:479–493 (1977).
Doi et al., Molecular and Cellular Biology vol. 7:2:898–904 (1987).
Levine et al., The Journal of Biological Chemistry vol. 251:2:324–328 (1976).
Walz et al., Thrombosis Research vol. 11:893–898 (1977).
Poncz et al., Blood vol. 69:1:218–225 (1987).
Guzzo et al., Nucleic Acids Research vol. 15:1:380 (1987).
Barone et al., The Journal of Biological Chemistry vol. 263:16:8710–8715 (1988).
Waleh et al., Proc. Nat'l. Acad. Sci. USA vol. 82:8389–8393 (1985).
Griffin et al., Cytogenet Cell Genet vol. 45:67–69 (1987).
Green et al., Mol Cell Biol (In Press) (1989).
Deuel et al. Proc. Nat'l. Acad. Sci. USA vol. 74:6:2256–2258 (1977).
Heemstra Thrombosis Research 29:323–332 (1983).
Hiti-Harper et al. Science vol. 199:4332:991–992.

*Primary Examiner*—Robert A. Wax
*Assistant Examiner*—Dian Cook
*Attorney, Agent, or Firm*—William H. Benz

[57] ABSTRACT

The present invention provides for the purification from native sources or the cloning and expression of a variant form of platelet factor 4 and also provides recombinant DNA vectors and methods for the expression and recovery of the platelet factor 4 variant. Also provided are compositions and methods for modulating immune responses in mammals comprising immunomodulating effective amounts of platelet factor 4 variant.

16 Claims, 7 Drawing Sheets

FIG. 1

```
        Val Glu Val Ile Ala Thr Leu Lys Asn Gly Arg Lys
         *   *                   *
5' AGCTT GTC GAA GTG ATA GCC ACG CTG AAG AAT GGA AGG AAA
3'     A CAG CTT CAC TAT CGG TGC GAC TTC TTA CCT TCC TTT

Ile Cys Leu Asp Pro Asp Ala Pro Arg Ile Lys Lys Ile Val
 *   *   *               *   *   **
ATT TGC TTG GAC CCG GAC GCC CCG CGG ATC AAG AAA ATA GTT G    3'
TAA ACG AAC CTG GGC CTG CGG GGC GCC TAG TTC TTT TAT CAA CTTAA 5'
```

```
                        10         (1)        20                    30                             50
5'-AATTCGTTAA CATGGAAGCT GAAGAAGACG GTGACCTGCA ATGCCTGTGC
    GCAATT GTACCTTCGA CTTCTTCTGC CACTGGACGT TACGGACACG
                            (2)

60         (3)        70                    80         90                             100
GTTAAGACCA CTTCTCAGGT ACGTCCGCGT CACATCACTT CTCTGGAAGT
CAATTCTGGT GAAGAGTCCA TGCAGGCGCA GTGTAGTGAA GAGACCTTCA
                            (4)

110         (5)       120                   140         (7)       150
AATCAAAGCT GGTCCGCCACT GTCCGACTGC TCAGCTCTGA GCTACTCTGA
TTAGTTTCGA CCAGGCGTGA CAGGCTGACG AGTCGACTAG CGATGAGACT
                            (6)

XbaI
           160                   180         (9)       190                   200
AAAACGGTCG TAAAATCTGT CTAGACCTGC AAGCTCTGCT GTACAAGAAG
TTTTGCCAGC ATTTTAGACA GATCTGGACG TTCGAGACGA CATGTTCTTC
                            (8)                              (10)

220         (11)       230                    240
ATCATCAAAG AACACCTGGA ATCTTAATGA CTGCAGAAGC TTG
TAGTAGTTTC TTGTGGACCT TAGAATTACT GACGTCTTCG AACTTAA-5'
                                            (12)
```

```
       710            720            730            740            750            760            770
GAGGTTGGAG GTATCCATCT TTGTACCACC TCCTAGCCAA GGCAGGTGCC CCCAGCCTTT TGTTTTGTAA
                                                                    T rich 780            790            800            810            820            830            840
TCTTGGCTGG CCAGAGTCTG AGTCTTCATA GCAGTGTCTT AGCTCCTGCA CCACAGTTCC TCGCTGTCCA 850            860            870            880            890            900            910
CACCAGGCTT CCCGACTGGA AGGACAGTGG GACACAGTGACG GGGATAAAA GAAGCCTGGT GAGGCCAGGA
                                                         Promoter 920            930            940            950            960            970            980
GTCACTGCCT GCAGAACCCC AGCCCGACTT TCCCTGCGCA AGCCCGACTT CTGGGATCCT GCTGGAACCT CAGCTGCAAC
| Transcription Start 995                  1010                  1025
ATG AGC TCC GCA GCC AGG TCC CGC CTC ACC CGC GCC ACC CGC CAG GAG ATG CTG TTC
MET Ser Ser Ala Ala Arg Ser Arg Leu Thr Arg Ala Thr Arg Gln Glu MET Leu Phe 1040                  1055                  1070                                  1089            1099
TTC GCC TTC CTC CTC CTG CCA GTT GTC GTC GCC TTC GCC AGA G gtgagagca gaaaccaggc
Leu Ala Leu Leu Leu Pro Val Val Val Ala Phe Ala Arg 1109            1119            1129            1139            1149            1159            1169
tgggaggggcc agcagcggcg aggggggagtc cgggaagccc tggggctggg aggaatcctc taggatcatg
```

FIG. 3-2

```
     1179       1189       1199       1209       1219       1229       1239
atcgcagctg ctccttattgc gcgcgtgctg agtctgcggg tacagtgcca ggcactgcac gtgcacctcg 1249       1259       1269       1279       1289       1299       1309
ccacctgctc agcacaacct ctgtctgaga gaggtctgat ttacggctaa ggaaaagaaa gctgaaggta 1319       1329       1339       1349       1359       1369       1379
gtggaaaagg tccctaaagt atctctggct actcaggagt cacaactccc acccctcctc ctctcttact 1389       1399       1415       1430
cctcccttt cccccctcag CT GAA GCT GAA GAA GAT GGG GAC CTG CAG TGC CTG TGT GTG
                        Ala Glu Ala Glu Glu Asp Gly Asp Leu Gln Cys Leu Cys Val 1445            1460              1475              1490
AAG ACC ACC TCC CAG GTC CGT CCC AGG CAC ATC ACC AGC CTG GAG GTG ATC AAG GCC
Lys Thr Thr Ser Gln Val Arg Pro Arg His Ile Thr Ser Leu Glu Val Ile Lys Ala 1505              1520            1533       1543       1553
GGA CCC CAC TGC CCC ACT GCC CAA CTC AT gtgagtcc tcgcactgca tcagttagtg
Gly Pro His Cys Pro Thr Ala Gln Leu Ile 1563       1573       1583       1593       1603       1613       1623
ctcccgctcc gtgccctcc tgcccatccc tcccccttct aatgccattt gcaaacccaa ggactgaaag
```

FIG. 3-3

```
          1633       1643                                        1666                             1681
tcacgtctct tctcttttcc ctgccag A GCC ACG CTG AAG AAT GGG AGG AAA ATT TGC TTG GAT
                              Ala Thr Leu Lys Asn Gly Arg Lys Ile Cys Leu Asp 1696        1711                                                                  1748
CTG CAA GCC CTG CTG TAC AAG AAA ATC ATT AAG GAA CAT TTG GAG AGT TAG CTACTAGCTG
Leu Gln Ala Leu Leu Tyr Lys Lys Ile Ile Lys Glu His Leu Glu Ser 1758       1768       1778       1788       1798       1808       1818
CCTAAGTGTG CACTTTCAAT CTAACTGTCA AAGAATCTTC TGATGTTTGT ATTATCCTTC TTATATTATA 1828       1838       1848       1858       1868       1878       1888
TTAACAAAAT AAATCAAGTT GTGGTATAGT CAATCTATTT CTTAATAATA CTGCAAAAAT AATGCTGACA
Poly A 1898       1908       1918       1928       1938       1948       1958
CATCACAATT TCATATTTTA AAATTTCCAG AATTTTAAGC AAAAAGCATT ATGAAGGAAG GCTTGGTTTA 1968       1978       1988       1998       2008       2018       2028
ATAAAGACTG ATTTTGTTCA GTGTTATATG TTAGCTGATA CATATTTCTT CATTTATGTG ATTGCAGTAC
Poly A                                                   GT Cluster 2038       2048       2058       2068       2078       2088       2098
TTTATAGCTA CATATTTACC TTGAATGTTA CAATTAGCTT GCCAATAAAT ATTAGTAGCT CTTAAGCATT
                                                      Poly A 2668       2678       2688       2698       2708       2718       2728
ACATCTGCAA AGATATATAT ATATATATAT ATATATATAT TTTTTTTTTT TCCCATGTTA AGCAACACAT
```

FIG. 4

```
          10'       20'        30'     ↓    6
      MSSAARSRLT RATRQEMLFL ALLLLPVVA FARAEAEEDG
      ****       * *  ****          *
      MSSAA---GF CASRPGLLFL GLLLLPLVVA FASAEAEEDG 16        26        36     ↓    46
      DLQCLCVKTT SQVRPRHITS LEVIKAGPHC PTAQLIATLK

DLQCLCVKTT SQVRPRHITS LEVIKAGPHC PTAQLIATLK 56        66
      NGRKICLDLQ ALLYKKIIKE HLES
              *        *    *
      NGRKICLDLQ APLYKKIIKK LLES
```

CLONING AND EXPRESSION OF A VARIANT GENE OF PLATELET FACTOR 4 AND COMPOSITIONS THEREOF TO MODULATE IMMUNE RESPONSES

DESCRIPTION

1. Technical Field

This invention is in the field of genetic engineering. More particularly, it relates to the cloning, expression, and microbial production of a variant gene of human platelet factor 4 (PF4var1). The invention also relates to compositions containing PF4var1 and to methods using such compositions to modulate immune responses in mammals.

2. Background Art

Platelets are circulating blood cells that function in the normal blood-clotting mechanisms in response to vascular injury. Platelet alpha-granules secrete a number of important proteins, including platelet factor 4 (PF4), platelet-derived growth factor (PDGF), connective tissue-activating peptide (CTAP-III), and transforming growth factor-beta (TGF-beta). Monocyte-derived neutrophil chemotactic factor (MDNCF), gamma-IP10, along with PF4 and CTAP-III, are members of a homologous multigene family of human proteins which share substantial amino acid sequence homology, including conservation of the four cysteine residues that form the two disulfide bonds in the mature protein.

Although the biological roles of these factors are not well defined, four of their most important properties are (a) the ability to stimulate DNA synthesis and cell division, and thus to act as potent mitogenic agents; (b) the ability to stimulate a variety of metabolic activities in connective tissue cells, including glucose transport, glycolysis, prostaglandin E2 and cyclic AMP formation, hyaluronic acid and glycosaminoglycan synthesis, and formation of plasminogen activator; (c) the ability to attract cells of the immune system to sites of inflammation and to stimulate their function; and (d) the ability to bind with high affinity to sulfated glycosaminoglycans, important constituents of cell surfaces and connective tissue and mast cells.

Platelet factor 4 is a platelet-secreted protein with several biological functions, including procoagulation, antiheparin, immunoregulatory, and chemotactic activities. PF4 has been demonstrated to be a potent chemotactic agent for monocytes and neutrophils (Deuel, et al. (1981) *Proc Natl Acad Sci USA* 78:4584), to bind serotonin (Heemstra, V. L. (1983) *Thrombosis Res* 29:323), to inhibit collagenase (Hiti-Harper, J., et al. (1978) Science 199:991), to reverse immunosuppression in animals (Katz, I. R., et al. (1986) *Proc Natl Acad Sci USA* 83:3491), and to inhibit the growth of some tumors (Taylor, S. and Folkman, J. (1982) Nature 297:307). PF4 has been isolated from both bovine, rat and human blood and purified to homogeneity (Wu, V. Y., et al. (1977), *Prep Biochem* 7:479; Doi, T. et al. (1987) *Mol Cellular Biol* 7:898; and Levine, S. P., and Wohl, H. (1976), *J Biol Chem* 251:324, respectively) and its amino acid sequence and physiochemical properties have been determined (see for example, Walz, D. A., et al. (1977), *Throm Res* 11:893). Recently, the DNA sequence from cDNA derived from a human erythroleukemic cell line was disclosed by Poncz, M., et al. (1987), *Blood* 69:219; this sequence encodes a full-length leader sequence of 30 amino acids preceded by an initial methionine residue and followed by the coding region for the 70 amino acid mature protein.

Guzzo, C., et al. (1987), *Nuc Acid Res* 15(1):380, reported an EcoRI polymorphism in the human PF4 gene, with an invariant band at 10 kb and a polymorphic band at either 5 or 3.1 kb. Yet to date, there have been no reports of naturally occurring variant forms of the PF4 gene or protein.

Earlier studies used PF4 obtained from platelets, a method of isolation that would be impractical for generating large amounts of the wild type or variant protein. Barone, A. D. et al. (1986) *J Biol Chem* 263(16):8710–8715 report the bacterial expression of PF4; however, PF4 was generated as a fusion protein with no means provided to isolate PF4 in its native form.

U.S. Pat. No. 4,702,908 discloses compositions of PF4 and methods using such compositions for immunomodulatory or immunoregulatory therapy. The studies documenting the various immune functions of PF4 were performed using PF4 isolated from platelet releasate and purified by affinity chromatography using heparin-agarose as the absorbent.

One object of the present invention is to provide the means for producing a newly discovered naturally occurring PF4 variant of the protein via recombinant DNA technology. These means include the use of the cDNA or a synthetic gene encoding PF4var1 that is designed for expression of PF4var1 in recombinant hosts. Also provided are expression vectors containing the PF4var1 gene fused to modified colicin E1 structural gene regions.

Another object of the invention is to provide PF4var1 for use therapeutically to prevent immune suppression, to restore the immune response in patients having a disease associated with immunosuppression, and to stimulate the normal immune response in patients challenged by antigen.

DISCLOSURE OF THE INVENTION

The present invention provides an isolated, cloned recombinant or synthetic nucleic acid sequence encoding a variant of platelet factor 4. This gene is characterized by the PF4var1 coding sequence as shown in FIGS. 2 and 3. The invention further provides the tools for synthesis and manipulation of the protein encoded by this sequence.

In one aspect, the invention relates to recombinant or synthetic nucleic acid sequences which encode the PF4var1 protein, and biological derivatives thereof. In other aspects, the invention relates to recombinant vectors bearing these nucleic acid sequences which can be used to transform cells, and to the recombinant proteins produced by these transformed cells.

Another aspect of the invention relates to a composition having immunomodulatory activity comprising as an active ingredient an amount of PF4var1 effective to modulate immune responses in a mammal. In other aspects, the invention is directed to a method for modulating immune response in a mammal in need of such treatment which method comprises administering to said mammal an amount of PF4var1 effective to modulate the immune response in said mammal.

Yet further aspects of the invention relate to a method for the bacterial production of platelet factor 4 variant 1, which method comprises:

a) culturing *E. coli* transformed with the above-described expression vectors;

b) disrupting the cultured transformants;
c) purifying the fusion protein from other cellular proteins;
d) cleaving the fusion protein at the specific cleavage site; and
e) recovering platelet factor 4 variant 1 from the cleaved products of step (d).

Still other aspects of the invention are directed to the protein product of the foregoing method.

BRIEF DESCRIPTION OF THE DRAWINGS

FIG. 1 is the sequence of the four DNA oligomers used to construct the probe that detected the PF4var1 gene. The amino acid sequence given is for a portion of CTAP-III and the asterisks denote the bases that were changed from the human PF4 cDNA sequence to match the CTAP-III amino acid sequence. A line is drawn through the junction of the four DNA oligomers.

FIG. 2 illustrates the synthetic DNA sequence synthesized for the expression of PF4var1. The 12 oligonucleotides used to create the entire coding sequence of PF4var1, bounded by two EcoRI linker sequences, are depicted by the arrows above the DNA sequence.

FIG. 3 is the sequence of the portion of the EcoRI fragment containing the natural human PF4var1 gene. The numbering is based on the entire 3201-basepair (bp) fragment length. Intron sequences are in lower case. The amino acid sequence is shown below the DNA. The arrow denotes the expected cleavage site for the PF4var1 leader sequence and the underlined amino acid residues are those which differ from the mature (processed) PF4 sequence.

FIG. 4 shows a comparison between human PF4 and PF4var1. Arrows indicate the positions of the introns.

MODES OF CARRYING OUT THE INVENTION

Figure 5:
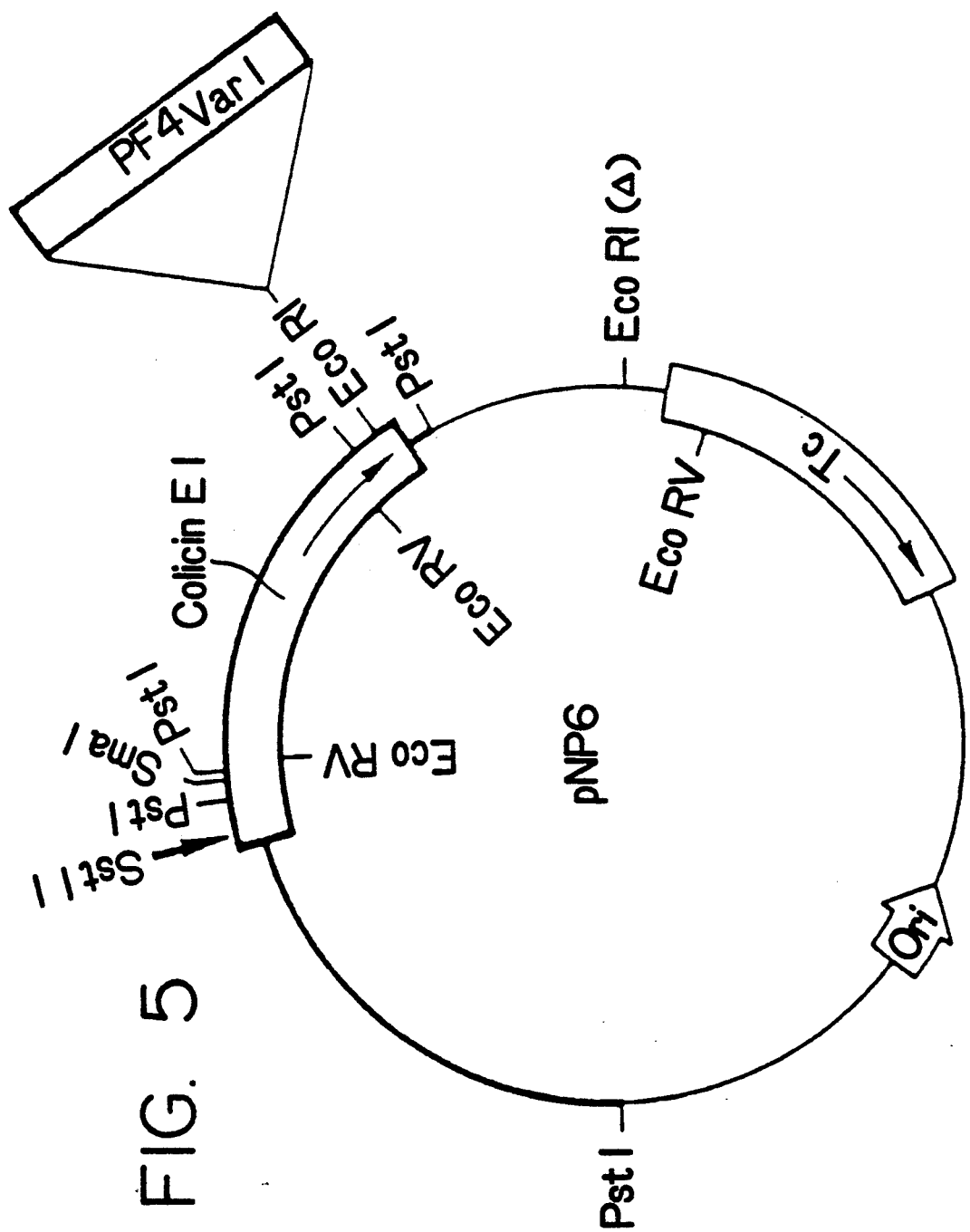
FIG. 5 is a restriction site and function map of plasmid pNP6deltaEcoRI that is used in making an expression vector containing the synthetic gene of FIG. 2.

The invention provides DNAs encoding the PF4var1 protein which has useful procoagulation, antiheparin, immunomodulatory and chemotactic activities. The protein may be purified from human tissue or recombinantly produced and supplied in sufficiently pure amounts to permit the design of both diagnostic and therapeutic applications.

One method of the invention comprises PF4var1 production in the form of fusion proteins in which a portion of the protein is a biologically inactive colicin E1 fragment containing a selective cleavage site within the fusion site such that the desired protein is readily cleavable. Such proteins may be produced using bacterial expression vectors in which the PF4var1 gene with a suitable translational terminator is inserted into a vector containing the colicin expression control sequence and part of the colicin structural gene at a convenient restriction site near the carboxy terminal end of the colicin structural gene. Due to PF4's high affinity for glycosaminoglycans, especially to heparins, heparin and chondroitin-sulfate can be used successfully for the affinity chromatographic isolation of the free PF4var1.

As used herein the term "platelet factor 4" refers to the 70 amino acid protein substantially corresponding to the mature protein described by Poncz et al. (1987), supra, and having any of the biological activities associated with PF4 such as the afore-described immunostimulatory, chemotactic and heparin neutralization activities.

As used herein, the term "PF4var1 protein" refers to the mature form of the human protein sequence (residues 1-70) provided in the top line of FIG. 4 and is intended to include all sources of the protein, including native, recombinant and chemically synthesized proteins. The term "precursor form of PF4var1" includes the leader sequence as shown in FIGS. 3 and 4. The term "PF4var1 gene" is defined as the nucleic acid sequence encoding the PF4var1 protein and includes nucleic acid sequences having silent mutations, so long as the corresponding amino acid remains the same. While the human genomic gene has been cloned, the source of the gene is not limited to specific mammalian species, although human is a preferred embodiment.

"Operably linked" refers to a juxtaposition wherein the components are configured so as to perform their usual function. Thus, control sequences or promoters operably linked to a coding sequence are capable of effecting the expression of the coding sequence.

"Control sequences" refers to a DNA sequence or sequences which are capable, when properly ligated to a desired coding sequence, of effecting its expression in hosts compatible with such sequences. Such control sequences include at least promoters in procaryotic hosts, and optionally, transcription termination signals. Additional factors necessary or helpful in effecting expression may also be identified. As used herein, "control sequences" simply refers to whatever DNA sequence may be required to effect expression in the particular host used.

The term "expression vector" includes plasmids, cosmids or phages capable of synthesizing a protein encoded by the respective recombinant gene carried by said vector. Such vectors are independently replicated in or capable of integration into the chromosome of an appropriate host cell for expression of the desired protein.

"Cells" or "cell cultures" or "recombinant host cells" or "host cells" are often used interchangeably as will be clear from the context. These terms include the immediate subject cell, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce recombinant PF4var1.

"Purified" or "pure" refers to material which is free from substances which normally accompany it as found in its native state. Thus, "pure" PF4var1, for example, refers to PF4var1 which does not contain materials normally associated with its in situ environment in human tissue. Of course, "pure" PF4var1 may include materials in covalent association with it, such as glycoside residues.

Modifications to the primary structure itself by deletion, addition, or alteration of the amino acids incorporated into the sequence during translation can also be made without destroying the biological activity of this variant protein, particularly the reduced heparin-binding activity of PF4var1. Such substitutions or other alterations result in proteins having an amino acid sequence which falls within the definition of proteins "having an amino acid sequence substantially equivalent to that of PF4var1".

As is the case for all proteins, the precise chemical structure of the PF4var1 protein of the invention depends on a number of factors. As ionizable amino and carboxyl groups are present in the molecule, the protein may be obtained as an acidic or basic salt, or in neutral form. All such preparations which retain their activity when placed in suitable environmental conditions are included in the definition of PF4var1. Further, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes. Certain aspects of such augmentation are accomplished through post-translational processing systems of the producing host; other such modifications may be introduced in vitro. Further, individual amino acid residues in the chain may be modified by oxidation, reduction, or other derivatization. Such alterations which do not destroy activity do not remove the protein sequence from the definition.

"Immune modulation" as used herein refers to one or more aspects of restoration of suppressed immune responses, inhibition of immune suppression (due to exposure of or administration to a mammal of an agent that causes suppressor cell activation), and augmentation of normal immune responses.

Gene Retrieval

The general strategy whereby the illustrated PF4var1-encoding sequence was obtained herein is as follows. A synthetic DNA probe designed to detect coding sequences for PF4 and CTAP-III was used to identify several similar sequences in total human DNA. This probe was similar to the PF4 gene sequence except for the minimum changes necessary to allow codon match with the CTAP-III amino acid sequence. Because of extensive homology between the two proteins, the resultant 78 base sequence has 42 contiguous nucleotides that were presumed to be a perfect match for the PF4 gene, assuming the absence of an intron.

Several bands were detected upon hybridization of the labeled DNA probe to nitrocellulose blots of restriction enzyme digests of the human genomic DNA. The EcoRI digest showed particularly strong hybridization signals corresponding to two fragments approximately 3 and 10 kilobases (kb) long. Sequence analysis of a corresponding 3201-basepair EcoRI fragment isolated from a human leukocyte genomic library in an M13 cloning vector demonstrated the existence of a variant of PF4.

The PF4var1 gene consists of three exons and two introns as shown in FIG. 3. The first intron is 328 basepairs (bp) long and separates a possible leader peptide (exon 1, amino acid residues 1'-34') from the beginning of the mature coding sequence defined by the known structure of the PF4 protein isolated from activated platelets. The 34-amino acid hydrophobic leader sequence encoded by exon 1 has 70% sequence homology with the leader sequence for PF4 but, in contrast, contains a hydrophilic amino-terminal region with four arginine residues.

The second intron is 128 bp long and divides exon 2 (amino acid residues 1-41) and exon 3 (residues 42-70). Exon 2 codes for a 42 amino acid segment that is 100% identical with the corresponding segment of the mature PF4 sequence containing the amino-terminal and disulfide-bonded core regions. Exon 3 codes for the 28-residue carboxy-terminal region corresponding to a domain specifying heparin-binding and cellular chemotaxis. This region contains three amino acid differences from PF4 as illustrated in FIG. 4.

A synthetic gene encoding the PF4var1 protein was assembled using known chemical synthesis techniques and cloned into an *E. coli* expression vector as described in the following examples.

Protein Expression

The cloned genomic, cDNA or synthetic DNA sequences can be expressed in appropriate expression systems. Of course, for the DNA gene sequence disclosed herein, the foregoing protocol for retrieving the gene need not be repeated, but conventional chemical synthesis methods can suitably be employed straightaway.

In U.S. Ser. No. 143,731, filed Jan. 14, 1988, by one of the co-inventors of the present invention, it is disclosed that various attempts were made to express the cloned PF4 gene using recombinant DNA techniques, including the direct expression of PF4 (i.e., not fused to another peptide sequence) in a bacterial host. Using a colicin E1 expression system identical to that used for CTAP-III expression (described in PCT Publication No. WO85/01067), significant levels of PF4 were not obtained. This was surprising in light of the fact that CTAP-III is highly homologous to PF4 sharing approximately 75% identity in nucleotide sequence and 65% identity in amino acid sequence. Thus, in one embodiment of the present invention, a fused gene construct similar to the gene fusion described in the above-referenced patent application is employed to reproducibly express the PF4var1 gene.

The fused gene construct is joined with an appropriate expression vector such that the fused gene is flanked at the 5'-end with transcriptional initiation regulatory sequences and at the 3'-end with transcriptional and translational termination sequences. (5'- and 3'- intend the direction of transcription).

After preparing the plasmid DNA for introduction into an appropriate host, the host is transformed, cloned, and individual clones selected for efficient expression by assaying for production of the desired product, e.g., PF4var1. As exemplified in the present invention, production of PF4var1 means that the level of expression of the PF4var1 fusion protein is at least 10% of total cellular protein. Screening can be efficiently performed using Western blots (antibody detection of product) of host cell colonies transferred to filters of nitrocellulose or other suitable material. Alternatively, by analyzing samples using gel electrophoresis an immediate and direct comparison can be made of which clones are most efficiently expressed by visualization of protein staining intensity, autoradiography or Western blotting of the product band. This screening procedure will usually be sufficient, although more quantitative immunoassays or enzyme assays can be employed, as appropriate.

Protein Purification

In preferred embodiments of the invention, the DNA insert encodes truncated colicin E1 proteins fused to PF4var1. In these embodiments, the colicin E1 gene encodes a protein which has a hydrophobic segment (approximately 30 amino acids), a physical chemical characteristic which facilitates the purification of the fusion protein from other cellular components. This hydrophobic segment allows contaminating proteins to be selectively extracted from the fusion protein using high salt concentrations (such as 1M guanadinium hydrochloride) and provides colicin E1-PF4varl fusion proteins greater than 50% pure.

After the fusion protein is partially purified, PF4varl is separated by subjecting the fusion protein to a chemical or enzymatic reaction that cleaves the protein at the fusion site. For instance, when the two segments of the protein are fused via a methionine residue, the protein may be treated with cyanogen bromide.

Protein Characteristics

FIG. 4 shows an amino acid sequence comparison between human PF4 and PF4varl. The sequences have been aligned for maximum similarity and the arrows indicate the positions of the introns. The greatest variation between the two proteins occurs in the leader sequence, residues 1'-34', which in PF4varl includes a three-codon insert in the middle of the sequence. Whereas this region is generally hydrophobic, which is characteristic of a secretory peptide, PF4varl shows major sequence diversity from PF4, particularly in the region between residues 6 and 17, where it has a much greater positive charge due to three additional Arg residues.

PF4varl has three amino acid differences in the mature protein sequence compared with PF4: $Pro_{58} \rightarrow Leu$, $Lys_{66} \rightarrow Glu$, and $Leu_{67} \rightarrow His$. The nature of these changes, all located in the carboxy-terminal region of PF4varl, may have a significant effect on the structure and function of PF4varl. For example, the carboxy-terminal region of PF4varl is less positively charged ($Lys_{66} \rightarrow Glu$), which reduces its ability to bind heparin as deduced by heparin-affinity chromatography studies of the recombinant protein.

While not wishing to be bound by any particular theory, it is believed that the reduced heparin affinity of the PF4varl protein may permit both altered cell binding specificity and a decrease in the adsorption to the vascular endothelium and the extracellular matrix.

The $Pro_{58} \rightarrow Leu$ change may also have a major effect on the protein's secondary structure. Assuming that human and bovine PF4 have essentially the same three-dimensional structure, the carboxy-terminal helix in human PF4 starts at $Pro_{58}$. Proline is a helix breaker; the change to leucine could extend the helix in the amino-terminal direction and alter the turn at positions 55-57 that links the helix to the third strand of beta-sheet. The $Leu_{67}$ to His change could also significantly alter the characteristics of the carboxy-terminal helix. $Leu_{67}$ which lies between the helix and the hydrophobic surface of the beta-sheet, is buried and surrounded by hydrophobic residues. Histidine at this position, especially if it is protonated, will weaken the packing of the helix against the sheet. To some extent, substitutions in PF4varl make its carboxy-terminal helix more like that of CTAP-III, in which only three of the four lysines are on one face of the helix due to an insertion of a glutamine between the corresponding positions 64 and 65 of PF4. This results in shifting a basic residue (lysine) into the positions corresponding to Leu $_{67}$ (PF4) or $His_{67}$ (PF4varl. Both PF4varl and CTAP-III show similarly reduced heparin-binding properties compared with those of either human or bovine PF4.

Compositions for Therapeutic Use

The purified PF4varl protein will typically be formulated with conventional pharmaceutically acceptable carriers for parenteral administration to mammals, for example, to stimulate the immune system. Suitable carriers include, but are not limited to, buffered isotonic human serum albumin solutions (see Remington's Pharmaceutical Sciences, 17th edition by Mack Publishing Company).

A preferred mode of administration of PF4varl for immunomodulatory purposes is by intravenous injection. The concentration of PF4varl that is effective for a particular therapeutic application varies depending on the severity of immune suppression, the amount and potency of the immunosuppressing agent whose effects are to be overcome by PF4varl, the weight of the mammal, and the schedule of administration. The minimum effective dose of PF4varl can be established by routine experimentation using serially diluted preparations of PF4varl.

Preferred PF4varl concentrations for treating humans will be within the range of about 5 ug to 10 mg/kg per treatment and that for mice is about 0.1 ug to 25 ug per animal. These dosage limits are broadly defined since the dosage regimen may vary according to the condition to be treated and the normal variance observed from mammal to mammal. For example, when PF4varl preparations are used as a vaccine adjuvant, one treatment will be necessary before or after or simultaneously with the vaccination. When used to combat immune suppression, one or more additional treatments might be necessary at appropriate intervals if the immune suppression persists or recurs.

PF4varl may be administered topically, for example, to stimulate wound healing at a desired site using conventional topical formulations such as creams, pastes, gels, sprays, ointments, and salves. Carriers used in such formulations are well known and include, without limitation, petrolatum, polyethylene glycol, gelatin, isopropyl myristate, polyvinyl alcohol, and the like. Alternatively, the purified PF4varl protein may be administered using controlled release dosage forms which typically consist of bandages or skin patches that contain the PF4varl in a manner such that it is released at a controlled rate to the skin. The control mechanism may be diffusion, osmosis, dissolution, erosion, or iontophoresis. The topical formulation of PF4varl may contain minor amounts of additives such as emollients, stabilizers, surfactants, skin penetration altering agents, and pigments. The concentration of PF4varl in the formulation will be correlated to the prescribed dose and surface area being treated. The concentration will normally be in the range of 0.0001% to 1% by weight of the dosage form. In any event, the amount administered is sufficient to produce the desired pharmacological effect, e.g., chemotaxis, etc., so as to facilitate wound healing.

The following provides a detailed description of specific embodiments of the invention that involves PF4varl, fusion proteins composed of colicin E1 fragments and PF4varl, and the purification of native and bacterially produced PF4varl. Immunostimulatory properties of PF4varl are also described.

EXAMPLES

Hybridization Probe Construction

Based on the known sequence of the mRNA of PF4 and reverse translation analysis of the amino acid sequence of CTAP-III, a DNA probe was designed to detect the genes for both proteins. This probe was similar to the PF4 gene sequence except for the minimum changes necessary to allow the codons to match the CTAP-III amino acid sequence. Because of extensive homology between the two proteins, the resultant 78 base sequence had 42 nucleotides that were presumed to be a perfect match for the PF4 gene, assuming the absence of an intron in this region. The synthesis of oligonucleotides shown in FIG. 1 was performed on an Applied Biosystems 380A synthesizer using 0-methylphosphoramidite chemistry. All reagents were from Beckman Instruments, Inc. The hybridization probe was constructed by ligating the four oligonucleotides and cloning them into the HindIII and EcoRI sites of an M13mp19 vector, as described below.

Radioactive Labeling

Radiolabeled probe was prepared by using the large fragment of DNA polymerase I (Klenow) to synthesize a strand complementary to the inserted probe sequence of the M13 single-stranded template in the presence of $^{32}P$-labeled nucleoside triphosphates. A fivefold excess of the M13 primer (GGGTAACGCCAGGGTTTT) was incubated with the template (2 ug/ul) at 55° C. for five minutes, then cooled to room temperature and incubated in 10 MM Tris-HCl, pH 7.5, 50 mM NaCl, 10 MM $MgCl_2$, 1 mM dithiothreitol, 30 uM each of dGTP, dATP, and dTTP, 3 uM [alpha-$^{32}P$]-dCTP (800 Ci/mmol, New England Nuclear), and 0.1 unit/ul Klenow polymerase (Bethesda Research Laboratories) for 60 minutes. The partially double-stranded template was then cleaved with HindIII. The single-stranded probe was purified by electrophoresis on a 5% polyacrylamide-7M urea gel. The radiospecific activity of the probe was approximately $10^9$ cpm/ug.

Southern Hybridization Analysis and Screening of a Genomic Library

The probe was hybridized to human genomic digests blotted onto nitrocellulose filters (Maniatis, T. et al., (1982) Molecular Cloning, Cold Spring Harbor, New York) in a buffer adapted from Amasino, R. M., [(1986) Anal Biochem 152:304–307], containing 20% formamide, 10% poly-ethylene glycol, 0.25M $Na_2PO_4$, pH 7.2, 0.25M NaCl, 7% sodium dodecyl sulfate (SDS), and 1 mM EDTA at 42° C. overnight. The filter was washed in 0.1×SSC (0.15M sodium chloride, 0.015M sodium citrate) and 0.1% SDS at 40° C. Several bands were detected. The EcoRI digest showed particularly strong hybridization signals corresponding to two fragments approximately 3 and 10 kb long.

Approximately 300,000 plaques from a human leukocyte genomic library in an EMBL lambda vector (Clonetech Laboratories, Inc.) were blotted onto nitrocellulose and hybridized with the probe under the same conditions described for Southern analysis. Positive plaques were picked and rescreened to obtain a pure clone.

DNA Sequence Analysis

DNA isolated from a positive clone was digested with EcoRI, and the 3.2 kb band that hybridized to the probe was subcloned into M13 vectors for sequence analysis by the dideoxy nucleotide method (Messing, J. et al., (1981) Nuc Acids Res 9:309–321). The promoter, coding, and intron regions were sequenced from both strands. Computer analysis of nucleic acid and protein sequence data was performed using programs available through the BIONET National Computer Resource for Molecular Biology.

Gene Construction

The synthetic gene for PF4var1 consists of 243 base pairs of DNA that are assembled from two major subfragments (designated I and II) composed of eight and four oligonucleotides, respectively. The 12 oligonucleotides were synthesized on an Applied Biosystems DNA Synthesizer using phosphoramidite chemistry.

The 12 synthetic oligonucleotides were purified, characterized, and ligated to produce fragments I and II as described below and as illustrated in FIG. 2.

Oligonucleotide Purification and Characterization

1. Purification

Polyacrylamide gels (12%) were prepared with 7M urea, 90 mM Tris-borate, and 2 mM EDTA buffer. Sample wells were formed with a comb having teeth at least 2 cm wide. After standing for 3 hours, the gel was preelectrophoresed for ~30 minutes Equal volumes of 1 to 5 $A_{260}$ units of the unpurified oligonucleotide sample and 7M of urea were mixed in 10 mM Tris-HCl buffer, pH. 7.5. The DNA sample was added to the gel, and a dye mixture (0.17% Bromphenol blue, 0.27% xylene cyanol, 10 mM Tris-HCl, pH 7.5) was added to one of the wells to monitor the migration rate of the oligonucleotides. Electrophoresis was performed at 400 to 600 volts until the Bromphenol blue migrated ~30 cm from the top of the gel. Both plates were removed, the gel was wrapped in plastic wrap, and the DNA was visualized using shortwave UV light. The desired band was carefully cut out using a razor blade. The piece of gel was placed in an Eppendorf tube and crushed with a glass bar. Then, 0.5 ml of TE (10 mM Tris-HCl, 1 mM EDTA, pH 7.5) was added to the tube, which was rotated overnight for DNA extraction. The tube was centrifuged at 15,000 rpm for 10 minutes, and the supernatant was recovered. The DNA sample was diluted 10 times with TE and was added to a C-18 Sep-Pak column (prepared using 10 ml of 100% acetonitrile and 20 ml $H_2O$) for desalting. Recovery of DNA was generally between 50 and 80%. The eluate was lyophilized and then resuspended in 0.5 ml $H_2O$.

2. End-Labeling, Gel El ectrophoresis, and Autoradiography

Ten pmole of the sample was lyophilized. The dried sample was dissolved in 1 ul of 10× concentrated kinase buffer (700 mM Tris-HCl, pH 7.6, 100 mM $MgCl_2$, 1 mM KCl, 50 mM dithiothreitol), 5 ul $H_2O$, and 1 ul T4 kinase solution containing at least 1 unit of activity. The sample was incubated for 30 minutes at 37° C. After the addition of 5 ul of the dye mixture, the sample was added to a polyacrylamide gel (20%, 0.4 mm thick, 15 cm long), electrophoresed until the Bromphenol blue migrated to the bottom of the gel, and autoradiographed by exposing the gel to X-ray film for 10 to 30 minutes.

3. Ligation of Oligonucleotides

Reaction mixtures for ligating oligonucleotides consisted of 50 mM Tris-HCl (pH 7.5), 10 mM MgCl$_2$, 20 mM dithiothreitol, 1 mM ATP, 100 pmole DNA (concentration of 5' ends), and 100 units of T4 ligase in a total volume of 100 ul. The reaction mixtures were incubated overnight at 16° to 21° C.

Ligation reactions were terminated by adding a 3× excess of EDTA to chelate the Mg$^{2+}$. Samples were heat denatured after adding urea and dye mixture and analyzed by gel electrophoresis.

FIG. 2 shows the 12 ligonucleotides used to construct the synthetic gene. Oligonucleotides 1 through 8 composed fragment I and 9 through 12 composed fragment II. These two fragments were assembled in vitro and cloned into the M13 vector as described below to confirm the DNA sequence.

Preparation of M13 Cloning Vector

The double-stranded replicative form (RF) DNA of M13 was prepared as follows. 2×YT broth was inoculated with E. coli JM101 cells infected by M13 and incubated overnight at 37° C. Cells were collected by centrifugation, washed, resuspended in buffer, lysed with lysozyme and Triton X-100, and treated with ribonuclease. Cellular debris was removed and RF DNA was purified using CsCl-ethidium bromide equilibrium centrifugation. The ethidium bromide was removed using n-butanol extraction. RF DNA was dialyzed and concentrated using ethanol precipitation.

Transformation System

Preparation of Competent Cells

E. coli was cultured in 2×YT broth until the OD$_{660}$ was between 0.6 and 0.7. Cells were collected by centrifugation, resuspended in 50 mM CaCl$_2$ (half of the culture volume), and kept on ice for 20 minutes. Cells were collected and resuspended in 1/10 volumes of CaCl$_2$.

Transformation

M13 RF DNA, which had been previously digested with endonucleases EcoRI and XbaI was ligated with the PF4varl fragments I or II and was mixed with competent JM101 cells and kept on ice for 20 to 40 minutes. The mixture was heat-shocked at 46° C. for 2 minutes and mixed with IPTG, Bluo-gal, soft agar (46° C.), and fresh growing JM101 cells. The mixture was plated on YT agar plates and incubated overnight at 37° C.

The JM101 cells that were transformed by intact M13 synthesized beta-galactosidase and produced blue plaques. Cells that were transformed by M13 containing a PF4varl fragment did not make beta-galactosidase and produced colorless plaques.

Nitrocellulose Filter Hybridization

The recombinant phage were screened for the presence of the PF4varl gene sequence as follows. Phage cultures were dot-blotted onto nitrocellulose filter paper using a BRL (Bethesda Research Laboratories) 96-well HYBRI-DOT TM manifold. The blotted phage were lysed, and the DNA was denatured and immobilized by washing the filters once with agitation for 15 minutes each in the following solutions: 0.5M NaOH; 0.5M Tris, pH 7.4; 2×SSC (0.3M NaCl, 30 mM sodium citrate), pH 7. Filters were washed briefly in 95% ethanol, air-dried, prehybridized for three hours, and hybridized overnight with $^{32}$P-labeled oligonucleotide at room temperature. Hybridized filters were washed twice in 1×SSPE with 0.1% SDS at 25° C. for 15 minutes each, dried, and autoradiographed. Then the filters were rewashed and probed with oligonucleotide 5'-GTAAAATCTGTCTAGACCTG-3', which corresponds to the junction between the PF4varl(I) and PF4varl(II) subfragments.

Isolation of ColE1 Plasmid

The following examples describe the construction of pNP6, an intermediate plasmid used to construct an E. coli expression vector for the production of PF4varl. The construction of pNP6 is also fully described in Waleh and Johnson (1985) Proc Natl Acad Sci USA 82:8389-8393 which is incorporated in its entirety by reference.

Strain JC411 (Col EL-D30) was grown in 60 liters of M9 medium (per liter: 1 g NH$_4$Cl, 6 g Na$_2$HPO$_4$·H$_2$O, 3 g KH$_2$PO$_4$, 5 g NaCl, 3 g casamino acids, 1 ml 10% MgSO$_4$ supplemented with 10 ml 20% glucose and 0.5 ml 1M CaCl$_2$ added after autoclaving) in a fermenter at 37° C. to a cell density of approximately 5×10$^8$ CFU/ml. Chloramphenicol was added to a final concentration of 100 ug/ml, and the incubation at 37° C. was continued for another 6 hours. Cells were recovered using a Sharpels continuous-flow centrifuge. Ten g (wet weight) of the pellet was suspended in 180 ml of 50 mM Tris-HCl buffer (pH 8.0) containing 50 mM EDTA and 15% sucrose. Then, 0.14 g of lysozyme was added, and the mixture was allowed to stand at room temperature for 10 minutes. Next, 16 ml of 10% SDS and 20 ml of 5M potassium acetate were added. The mixture was incubated on ice for 30 minutes and then centrifuged at 12,000 rpm for 30 minutes using the SS-14 rotor and a Sorvall centrifuge. Four mg of pancreatic ribonuclease A was added to the supernatant and the mixture was incubated at 37° C. for 1 hour. The sample was extracted twice with an equal volume of phenol saturated with 0.1M Tris, pH 8.0, and the DNA was precipitated by adding 1/10 sample volume of 3.0M sodium acetate and 2.5 volumes of cold ethanol, followed by an overnight incubation at −20° C. The resulting precipitate was recovered by centrifugation at 7,000 rpm for 50 minutes in a refrigerated Sorvall centrifuge using an HB-4 rotor. The pellet was dissolved in 50 ml of 10 mM Tris-HCl buffer (pH 7.5) containing 0.3M NaCl and 5 mM EDTA (NE buffer). This sample was then applied to a Bio-Gel A.5 column (Bio-Rad Laboratories, Richmond, Cal.), 5×100 cm, equilibrated with NE buffer. The DNA was eluted with NE buffer. Twenty-ml fractions were collected at a flow rate of 60 ml/hr. The elution of DNA was monitored by measuring the absorbance of each fraction at 260 nm using a Gilford 2600 UV-VIS spectrophotometer. The host DNA and the plasmid DNA were recovered together in the void volume. The fractions containing the DNA were pooled and precipitated with ethanol. The precipitate was collected by centrifugation at 8,000 rpm for 40 minutes in a refrigerated Sorvall centrifuge using an HB-4 rotor and redissolved in 5 ml 10 mM Tris-HCl buffer (pH 7.8) containing 0.2M NaCl.

The DNA sample was applied to an RPC-5 column, 0.9×90 cm, and packed under pressure at 30° C. The DNA was eluted with a linear gradient (total volume, 1 liter) of 0.6-0.7M NaCl in 10 mM Tris-HCl buffer, pH. 7.8. Fractions of 2.5 ml were collected at a flow rate of 0.8 ml/min. The elution of DNA was monitored by measuring the conductivity of each collected sample using a conductivity meter (Radiometer, Copenhagen), and by agarose gel electrophoresis using vertical agarose slab gels (0.25×14×15.5 cm). The samples were applied to 1% agarose gels prepared in 40 mM Tris base buffer, pH 8.2, containing 1 mM EDTA and 5 mM sodium acetate (TAE buffer), and electrophoresed for 3 hours at a constant applied voltage of 5 V/cm. Fractions containing the supercoiled and the nicked circular DNA were pooled separately and were precipitated with cold ethanol. The resulting precipitates of ColE1 DNA molecules were dissolved in 1.0 and 0.6 ml TEN buffer, respectively.

Isolation of Plasmid pBR322

Plasmid pBR322 was isolated from E. coli strain 294 (pBR322) by the procedure used for isolating ColE1 plasmid described above.

Preparation of Sheared Fragments of ColE1 DNA

Two hundred ul of nicked circular ColE1 DNA (0.7 ug/ul) and 2.8 ml of 0.3M sodium acetate were mixed. The DNA solution was placed in the microhomogenizer cell of an omnimixer (Dupont Instruments, Newton, Conn.), and the DNA was sheared at 38,500 rpm for 20 min. The temperature was kept at 0° C. throughout the shearing process. The sheared DNA was precipitated with ethanol, redissolved in 100 ul of TEN buffer, and treated with calf intestinal phosphatase (CIT) (Boehringer Mannheim, Indianapolis, In.). The treatment with CIT was carried out in two 500 ul reaction mixtures. Each reaction mixture contained 380 ul distilled water, 50 ul 1M Tris-HCl buffer (pH 8.0), 5 ul 10 mM zinc sulfate, 5 ul CIT (10 U/ul). After incubation at 37° C. for 30 minutes, an additional 5 ul of CIT was added and the incubation at 37° C. continued for another 30 minutes. The reaction mixtures were extracted twice with an equal volume of buffer-saturated phenol, and the DNA was precipitated with ethanol. The heterogeneous population of DNA fragments was further purified and separated according to size by sucrose gradient velocity centrifugation. A discontinuous sucrose gradient was prepared by sequential layering of 3.4 ml of 20%, 15%, 10%, and 5% sucrose in 0.3M sodium acetate buffer (pH 7.0) containing 1 mM EDTA in centrifuge tubes for the SW40 rotor (Beckman). The DNA sample in 100 ul (0.25 ug/ul) was layered on the sucrose gradient and centrifuged at 35,000 rpm for 20 hours at 10° C. using an L8-70 Beckman ultracentrifuge. Fractions of 0.5 ml each were collected and precipitated with ethanol. The precipitates were redissolved in 50 ul of TEN buffer and analyzed by agarose gel electrophoresis. DNA fragments generated by the treatment of bacteriophage DNA with HindIII endonuclease were used as molecular-weight standards. The lambda/HindIII reaction mixture contained 27 ul distilled water, 10 ul 5×HindIII buffer, 1 ul lambda DNA (0.7 ug/ul), and 2 ul HindIII solution (2 U/ul).

Sucrose gradient fractions, containing sheared CoLE1 DNA fragments averaging 2,000 bp, were pooled, precipitated with ethanol, and redissolved in TEN buffer.

Cloning of Sheared ColE1 Fragments in pBR322

Plasmid pBR322 was cleaved to linear molecules with PstI. The reaction mixture contained 520 ul distilled water, 200 ul 5×PstI buffer, 200 ul pBR322 DNA solution (0.25 ug/ul), and 80 ul PstI (12 U/ul), and was incubated at 37° C. for 4 hours. The reaction was stopped by adding EDTA to 20 mM and extracted with an equal volume of phenol. The DNA was precipitated with ethanol and redissolved in TEN buffer.

Poly(dG) homopolymer extensions were added to linear pBR322 molecules in a reaction mixture containing 5 ul distilled water, 20 ul 500 mM potassium cacodylate, 10 ul 10 mM cobalt chloride, 10ul 1 mM DTT, 2 ul 10 mM dGTP, 20 ul 3H-dGTP (New England Nuclear Corporation), 25 ul DNA (0.04 ug/ul), and 5 ul (12 U/ul) terminal deoxynucleotidyl transferase (Bethesda Research Laboratories, Inc., Gaithersburg, Md.).

Poly(dC) homopolymer extensions were added to ColE1 sheared fragments in a similar reaction mixture, except that the total DNA was 2.0 ug and the nucleotide triphosphate was dCTP. The above reactions were carried out at 37° C. for 2 and 3 minutes, respectively, and were stopped by adding EDTA to 20 mM and extracting with phenol. ColE1-[poly(dC)]fragments were redissolved in 115 ul distilled water and were annealed to linear pBR322-[poly(dG)] molecules by adding 40 ul 0.5M NaCl, 40 ul 50 mM EDTA (pH 7.25), and 3 ul linear pBR322-[poly(dG)] DNA solution (0.1 ug/ul). The annealing mixture was incubated at 70° C. for 15 minutes and then cooled to 40° C. over a 5-hour period. The mixture was kept at 45° C. overnight, then cooled to room temperature.

For transformation into E. coli 294, an overnight culture grown in L-broth was diluted 1:100 into fresh L-broth medium and incubated with shaking at 37° C. until the $OD_{600}$ was 0.6. At this time, 35 ml of culture was centrifuged at 6,000 rpm for 120 minutes at 4° C., and the pellet was resuspended in 20 ml 0.05M $CaCl_2$. The cells were incubated on ice for 15 minutes before they were collected by centrifugation at 4,000 rpm for 10 minutes. The cells were resuspended in 4 ml 0.05M $CaCl_2$ and mixed with 200 ul of a DNA solution prepared by adding 50 ul of the annealing mixture and 150 ul 10 mM Tris-HCl (pH 7.5) containing 10 mM $MgCl_2$ and 10 mM $CaCl_2$. This mixture was incubated at 0° C. for 25 minutes, followed by incubation at 50° C. for 10 seconds and at room temperature for 10 minutes. At this point, 14 ml of L-broth was added and the culture was shaken at 37° C. for 30 minutes. Then, 480 ul of tetracycline solution, 1.25 mg/ml, was added to the culture, and the incubation was continued for another 30 minutes. Aliquots of 100 ul were plated on freshly prepared agar plates containing 25 ml L-broth, 1.5% agar and 25 ug/ml tetracycline. The tetracycline resistant ($Tc^4$) transformants were further tested for sensitivity to ampicillin ($Ap^s$) by plating on agar containing 25 ug/ml ampicillin.

The $Tc^4$ $Ap^2$ transformant colonies were then screened for the spontaneous production of colicin. Single colonies were spotted on L-agar plates and were incubated at 37° C. overnight. The colonies were killed by exposing them to chloroform vapor, then overlaid with 5 ml L-broth containing 0.7% agar and 0.1 ml of an overnight culture of E. coli K-12, CL142. After the agar was allowed to harden, the plates were incubated at 37° C. overnight. Colonies with a zone of inhibition around them were scored as colicin producers (Col+).

The $Tc^4$ $Ap^s$ Col+transformant colonies were screened for the presence of recombinant plasmids by analyzing a small amount of cleared lysate by agarose gel electrophoresis. The size of the plasmids was determined by measuring the electrophoretic migration of DNA through an agarose gel using 8 plasmid standards, ranging in size from $1.36 \times 10^6$ to $35.8 \times 10^6$ daltons (Marcina, F. L., et al (1978), Plasmid 1:417-420).

Restriction Endonuclease Fragment-Size Analysis of Recombinant Plasmids

Transformed clones were grown in 2-liter cultures. Cleared lysates were prepared as described above. The supernatants were treated with pancreatic RNase A (100 ug/ml at 37° C. for 30 minutes) and then were extracted with phenol. The DNA was precipitated with ethanol and redissolved in TEN buffer.

Restriction enzymes were obtained as commercial preparations from Bethesda Research Laboratories, Inc. (BRL). The DNA was digested with PstI, EcoRI, SmaI, and SacII, using the conditions specified by BRL. Samples were applied to 1% agarose gels and electrophoresed for 4 hours at a constant applied voltage of 5 V/cm. The molecule weights of restriction fragments were determined relative to the standard migration patterns of bacteriophage lambda DNA digested with HindIII and HaeIII.

Restriction analysis using PstI was used to establish the size of the fragment inserts in the PstI site of the pBR322 portion of the recombinant plasmids. FIG. 4 is a restriction map of the recombinant plasmid, designated pNP6, * f one of the transformed clones. A sample of this transformed clone, designated NP6-294, was deposited in the ATCC on Aug. 24, 1983. This sample was assigned ATCC accession no. 39418. This deposit was accepted under the Budapest Treaty and will be maintained and made accessible to others in accordance with the provisions thereof.

E. coli strain NP6-294 (pNP6) was grown and plasmid DNA was further purified by adjusting 500 ug of DNA to 3.9 ml of TEN buffer and adding 3.45 g CsCl and 0.1 ml ethidium bromide stock solution (5 mg/ml). The mixture was transferred into a cellulose nitrate tube for an SW50.1 rotor (Beckman) and centrifuged at 36,000 rpm at 10° C. for 40 hours. The plasmid DNA band was located under a longwave UV light and was removed with a syringe by puncturing the tube from the side. The DNA sample was extracted five times with butanol and dialyzed against 100 volume ($\times 3$) of TEN buffer for 24 hours at 4° C. The DNA was then precipitated with 2.5 volumes of ethanol and 1/10 volume of 3M sodium acetate.

Preparation of Derivative pNP6deltaRI

Plasmid pNP6 contains two EcoRI restriction sites, one located in the carboxy terminal region of the colicin E1 gene, the other located near the tetracycline resistance gene of the original pBR322 vector. A derivative of pNP6 lacking the second site was constructed as follows. pNP6 was digested with EcoRI under limited reaction conditions so that linear molecules (cleaved at only one of the two sites) were produced. Linear molecules of pNP6 were purified by agarose gel electrophoresis and subsequently reacted with DNA polymerase I and deoxyribonucleotide triphosphates to fill in the single-stranded ends. The resulting molecules were circularized in a blunt-end ligation reaction using $T_4$ ligase and then they were used to transform E. coli 294 as described previously.

Colicin-producing transformants were selected as described previously. DNA was isolated from individual clones and digested with EcoRI to identify those that contained a single, intact EcoRI site within the colicin gene. The location of the single EcoRI site was confirmed by additional restriction endonuclease mapping.

Preparation of pNP6-Col(504)-PF4

A synthetic, wild-type PF4 gene (coding for the protein shown in FIG. 4 and constructed as taught above for PF4varI) was removed from the M13 sequencing vector and cloned into the single EcoRI site of plasmid pNP6deltaRI. This recombinant DNA plasmid has the ability to produce a large protein (574 amino acids) that is a fusion of the PF4 protein (70 amino acids) with residues 1-504 of the colicin gene. Cells containing this plasmid were grown in culture and treated with mitomycin C to induce synthesis of the fusion protein.

Preparation of pNP6-Col(150)-PF4varI

There are three EcoRV restriction sites in pNP6-deltaRl; two are within the colicin E1 structural gene and the other is within the tetracycline gene as illustrated in FIG. 5. Approximately 1,000 basepairs of DNA were deleted from plasmid pNP6-Col(504)-PF4 using partial EcoRV digestion conditions. Since transformants are selected for $Tc^4$, only the desired transformants having the EcoRV fragment deleted from the colicin gene will result. The resulting plasmid codes for only 150 amino acids of colicin preceding the EcoRI site PF4 coding sequence, and contains a single methionine residue joining the colicin segment and PF4. The fusion of this colicin segment to the PF4 protein specifically enhances the recovery and purification procedure.

The EcoRI restriction fragment containing the synthetic gene encoding PF4varI was subcloned into EcoRI-digested pNP6-Col(150)-PF4. E. coli cells transformed with this plasmid were grown in culture and treated with mitomycin C to induce synthesis of the fusion protein.

E. coli 294 cells containing plasmid pNP6-Col(150)-PF4varI were reproducibly cultured in volumes (up to at least 12 liters) and upon induction with mitomycin C, produced the Col(150)-PF4varI medium fusion as approximately 20% of the total cellular protein.

Purification of PF4varI

Protein extracts were prepared from pNP6-Col(150)-PF4varI by sonication of induced cells in 1M guanidinium hydrochloride (GnHCl) or 25 mM Tris, 10 mM EDTA, 50 mM glucose, pH 8.0 (TEG). The fusion protein was found in the insoluble fraction. Following solubilization of the PF4varI fusion protein in 7M urea or 6M GnHCl, a sample of the protein was dialyzed extensively against distilled water in preparation for the CNBr cleavage reaction. The fusion protein precipitated during dialysis and was collected by centrifugation. The precipitate was lyophilized and then dissolved in 70% formic acid and reacted with a 100 to 1,000-fold molar excess of CNBr for 18 hours at room temperature.

The CNBr reaction mixture was lyophilized, resuspended in distilled water and lyophilized again. The protein mixture was dissolved in 0.05M Tris buffer, pH 8.2 containing 6M GnHCl. A reducing agent such as dithiothreitol or beta-mercaptoethanol was added to a final concentration of approximately 0.1M, and the mixture was incubated at a temperature between 20° and 37° C. for 1 to 4 hours. The resulting solution was then dialyzed against the same buffer but without reducing agent. The protein solution was adjusted to a PF4var1 concentration of approximately 0.2 mg/ml and a 2:1 mixture of oxidized and reduced glutathionine at a final concentration of 1 mM. The protein refolding reaction was allowed to proceed at room temperature for 10 to 20 hours, during which time it was dialyzed against 10 to 50 volumes of 0.05M Tris buffer, pH 8.2 containing 0.5M NaCl. These conditions result in greater than 80% of the PF4var1 forming the correct disulfide bonds and refolding to the native conformation.

Heparin-Affinity Chromatography

The refolding mixture was subsequently dialyzed against distilled water and lyophilized. The protein was then dissolved in GnHCl or NaCl or chondroitin sulfate at high concentration (>10 mg/ml protein), and diluted to an ionic strength of 0.2–0.4 just prior to purification by heparin affinity chromatography. Chromatographic columns were prepared using commercially available heparin agarose (Bio-Rad). Heparin may be substituted with other glycosaminoglycans such as chondroitin sulfate. Thus, as used herein, the use of the term "heparin" includes related compounds.

Protein was applied to the column in low ionic strength buffer at pH 6.5 and the column was eluted with a linear gradient of NaCl. Native recombinant PF4var1 eluted at a NaCl concentration of approximately 0.84M, compared to 1.3M for human, platelet-isolated PF4. Unfolded or incorrectly folded PF4var1 eluted at a significantly lower NaCl concentration, usually 0.3–0.4M NaCl or less. Purification to homogeneity is accomplished using reverse phase HPLC on a Vydak C-4 column using acetonitrile gradient elution (0–30%) at pH 2-3.

Recombinant PF4var1 prepared using this procedure was distinguishable from human PF4 as characterized by amino acid composition, heparin binding and immunostimulatory properties.

Purification of PF4var1 from Platelets, Cultured Cells or Tissue

Although the cell type(s) and tissue(s) of origin for PF4var1 have not yet been identified, the protein may be purified from mammalian sources by extraction from activated platelets or by homogenization of cultured cells and tissues using neutral buffers at moderate ionic strength (e.g., 50 mM Tris, 0.5M NaCl, pH 6.5–8.5), and/or by acid-ethanol extraction (e.g., 50–70% ethanol in 0.05M HCl) of platelet concentrates or disrupted cells. Subsequently the PF4var1 is purified as described above for the recombinantly produced protein using heparin affinity chromatography and HPLC.

Immunostimulatory Properties of PF4var1

Experimental immunosuppression can be studied by injecting mice intravenously (I.V.) with an immunosuppressive agent such as concanavalin A (Con A) together with sheep red blood cells (SRBC) and measuring the reduction in the production of antibody against SRBC using a plaque-forming assay. The suppression appears to be induced by the proliferation of T-cells of the suppressor phenotype caused by the Con A. Suppressor T-cells are antigen-specific cells that can suppress the function of antibody-producing B cells or other T-cell subsets. PF4var1 appears to restore the immune response by binding to activated peripheral suppressor T-cells.

The ability of PF4var1, PF4 and CTAP-III to reverse immunosuppression in mice was evaluated in dose response experiments in which either allogeneic lymph node cells (LNC) or Con A was used as the immunosuppressive agent. Three mice per group were injected I.V. with SRBC and LNC or Con A. Control mice were injected with SRBC alone. Five days later, the number of anti-SRBC antibody-producing cells in the spleens of mice were determined using the Cunningham plaque-forming cell assay (Mishell and Shirgi, in *Selected Methods in Cellular Immunology*, 3rd ed., pp. 69–77, 1980). The mice injected with LNC or Con A generally exhibit a 30–50% reduction (suppression) in the number of plaque-forming cells compared with that of mice injected with SRBC alone.

Table 1 compares the immunostimulatory properties from one set of animal studies of PF4var1, PF4 and the homologous platelet protein, CTAP-III at different levels of immunosuppression. Conclusions that may be drawn from animal studies reveal that both PF4var1 and PF4 can reverse immunosuppression compared to CTAP-III which has no significant activity under any of the conditions tested. As the level of immunosuppression decreases, the relative immunostimulatory effect of PF4 tends to decrease. In contrast, although PF4var1 exhibits a lower immunostimulatory effect at high levels of immunosuppression, it appears to show a much higher immunostimulatory effect at lower levels of suppression. The difference in the apparent immunostimulatory potency between PF4var1 and PF4 may be due primarily to their difference in heparin binding properties. PF4var1 may be more potent, at least under some conditions, because its reduced heparin affinity results in lower binding to the vascular endothelium and therefore greater bioavailability.

TABLE 1

Effect of hPF4, hPF4var1, and CTAP-III on Experimentally-Induced Immunosuppression in Mice

| Treatment of Mice | | | Mean PFC/Spleen per Conc. of Stimulant | | | |
|---|---|---|---|---|---|---|
| SRBC | ConA | Stim. | 1 μg | 2.5 μg | 5 μg | 10 μg |
| + | — | — | | | 45,000 | 45,500 |
| + | 50 μg | — | | | 4,470 | 1,500 |
| + | 50 μg | hPF4 | | | 168 | 13,400* |
| + | 50 μg | var1 | | | 4,400 | 1,460 |
| + | 50 μg | CTAP | | | 2,530 | 1,350 |
| + | — | — | 110,000 | 79,000 | 106,000 | 90,100 |
| + | 25 μg | — | 17,200 | 4,540 | 19,400 | 6,400 |
| + | 25 μg | hPF4 | 32,300* | 11,900* | 42,900* | 10,800* |
| + | 25 μg | var1 | 8,320 | 7,970 | 23,100 | 12,500 |
| + | 25 μg | CTAP | 9,260 | 2,720 | 27,400 | 8,790 |
| + | — | — | | | 75,800 | 91,800 |
| + | 10 μg | — | | | 22,600 | 78,400 |

TABLE 1-continued

Effect of hPF4, hPF4var1, and CTAP-III on Experimentally-Induced Immunosuppression in Mice

| Treatment of Mice | | | Mean PFC/Spleen per Conc. of Stimulant | | | |
|---|---|---|---|---|---|---|
| SRBC | ConA | Stim. | 1 µg | 2.5 µg | 5 µg | 10 µg |
| + | 10 µg | hPF4 | | | 60,800* | 169,000* |
| + | 10 µg | var1 | | | 121,000 | 165,000 |
| + | 10 µg | CTAP | | | 42,100 | 83,300 |
| + | — | — | 65,300 | 118,000 | 104,000 | 79,400 |
| + | 12.5 µg | — | 50,800 | 30,300 | 58,200 | 37,300 |
| + | 12.5 µg | hPF4 | 13,100 | 24,700 | 64,200* | 67,700* |
| + | 12.5 µg | var1 | 2,560 | 53,100 | 132,000 | 1,200 |
| + | 12.5 µg | CTAP | 432 | 30,100 | 24,100 | 25,300 |

CB6F1 mice were injected iv with various compounds or saline and were then injected 1 hour later with concanavalin A or saline. One day later, each mouse was injected ip with $5 \times 10^7$ sheep red blood cells. Five days later, the spleen of each mouse was removed and the number of anti-SRBC antibody producing cells determined by the Cunningham slide technique. Results are expressed as the geometric mean of three mice per group.

Modifications of the above-described modes for carrying out the invention that are obvious to those of skill in the technical fields related to the invention are intended to be within the scope of the following claims.

We claim:

1. An isolated, cloned recombinant or synthetic DNA sequence encoding a $Leu_{58}$, $Glu_{66}$, $His_{67}$ variant of platelet factor 4.

2. The DNA sequence of claim 1 which encodes the platelet factor 4 variant, characterized by th PF4var1 coding sequence represented by necleotides 15 to 224 of FIG. 2 or nucleotides 1402 to 1735 of FIG. 3.

3. The DNA sequence of claim 1 further comprising the leader sequence of FIG. 3.

4. The DNA sequence of claim 1 which is operably linked to a prokaryotic control sequence for expression.

5. The DNA sequence of claim 4 wherein the control sequence is from the colicin E1 promoter.

6. The DNA sequence of claim 4 which is ligated in translational reading phase with a second DNA sequence to create a fused gene wherein said second DNA sequence is derived from the colicin E1 structural gene.

7. A plasmid expression vector comprising the DNA sequence of claim 4.

8. A plasmid expression vector comprising the DNA sequence of claim 7.

9. The plasmid expression vector of claim 8 which is pNP6-Col(150)-PF4var1.

10. Recombinant prokaryotic host cells transformed with the plasmid expression vector of claim 7.

11. Recombinant prokaryotic host cells transformed with the plasmid expression vector of claim 8.

12. The recombinant host cell of claim 10 which is *E. coli*.

13. The recombinant host cell of claim 11 which is *E. coli*.

14. A method for the bacterial production of platelet factor 4 variant 1, which method comprises:
 a) culturing the *E. coli* transformants of claim 13;
 b) disrupting the transformants;
 c) purifying the fusion protein from other cellular proteins;
 d) cleaving the fusion protein at the specific cleavage site; and
 e) recovering the platelet factor 4 variant 1 from the cleaved product of step (d).

15. The method according to claim 14 wherein platelet factor 4 variant 1 is purified by heparin affinity chromatography.

16. The DNA sequence of claim 1 further comprising the leader sequence of FIG. 4.

* * * * *